US00PP27342P3

(12) United States Plant Patent
Van Swieten

(10) Patent No.: US PP27,342 P3
(45) Date of Patent: Nov. 1, 2016

(54) ***PHALAENOPSIS* ORCHID PLANT NAMED 'PHALDIQYK'**

(50) Latin Name: ***Phalaenopsis* hybrid**
Varietal Denomination: PHALDIQYK

(71) Applicant: ANTHURA B.V., Bleiswijk (NL)

(72) Inventor: Martinus Nicolaas Gerardus Van Swieten, The Hague (NL)

(73) Assignee: ANTHURA B.V., Bleiswijk (NL)

( * ) Notice: Subject to any disclaimer, the term of this patent is extended or adjusted under 35 U.S.C. 154(b) by 96 days.

(21) Appl. No.: 14/121,870

(22) Filed: Oct. 27, 2014

(65) Prior Publication Data

US 2016/0120089 P1 Apr. 28, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Upov Pluto Plant Variety Databse Mar. 24, 2016, retrieved on Mar. 30, 2016, retrieved from the Internet at <http://www.upov.int/pluto/en/index.jsp> one page.*
EU Community Plant Variety Rights, Official Gazette, 4.2014, Aug. 15, 2014, pp. 37 and 56.
EU Community Plant Variety Rights, Official Gazette, 3.2015, Jun. 15, 2015, p. 81.
EU Community Plant Variety Rights application No. 20141121, filed Apr. 25, 2014, 7 pp.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALDIQYK', particularly characterized by red-purple flowers with yellow at the base, 1 to 2 peduncles, inflorescence that is long and moderate, narrow oblong shaped leaves, and propagated by tissue culture is disclosed.

3 Drawing Sheets

Genus and species: *Phalaenopsis* hybrid.
Variety denomination: 'PHALDIQYK'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDIQYK'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicle, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDIQYK' is particularly characterized by its attractive and unique red-purple flowers with yellow at the base, economical propagation by tissue culture, rapid growth, and a plant dimension suitable for packaging and shipping to the market.

'PHALDIQYK' is a product of a planned breeding program conducted in Bleiswijk, The Netherlands.

The new *Phalaenopsis* 'PHALDIQYK' originated from a cross made in March 2005 in Bleiswijk, The Netherlands. The female parent is a yellow *Phalaenopsis* pot plant named '22286-0004' (unpatented), while the male parent is a pink *Phalaenopsis* pot plant named '08815-0001' (unpatented). A single plant was selected in March 2008 and has been asexually reproduced repeatedly by meristem tissue culture in Bleiswijk, The Netherlands over a 2.5-year period. The new variety has been found to retain its distinctive characteristics through successive asexual propagations.

Asexual reproduction of 'PHALDIQYK' by meristem tissue culture was first performed in October 2011 in Bleiswijk, The Netherlands and has demonstrated that the new cultivar is firmly fixed and retained through successive generations of asexual reproduction.

Plant Breeder's Rights for this variety have been applied for in Europe on Apr. 25, 2014. 'PHALDIQYK' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Red-purple flowers with yellow at the base;
2) 1 to 2 peduncles;
3) Inflorescence is long and moderate;
4) The shape of the leaves is narrow oblong; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in May 2014.

DESCRIPTION OF THE NEW VARIETY

Figure 1:
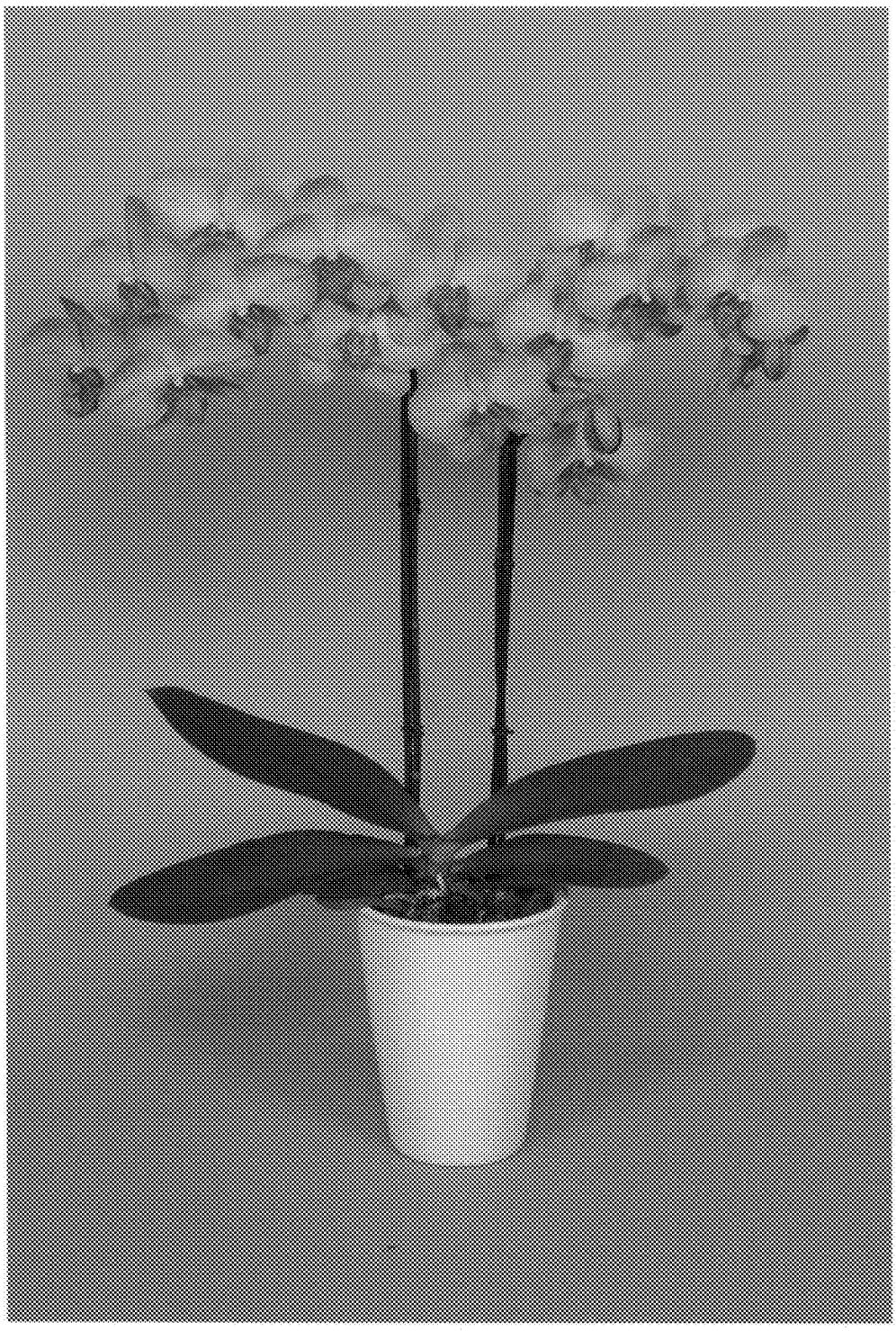
FIG. 1 shows the overall plant habit, including blooms, buds and foliage of 'PHALDIQYK'.
Figure 2:
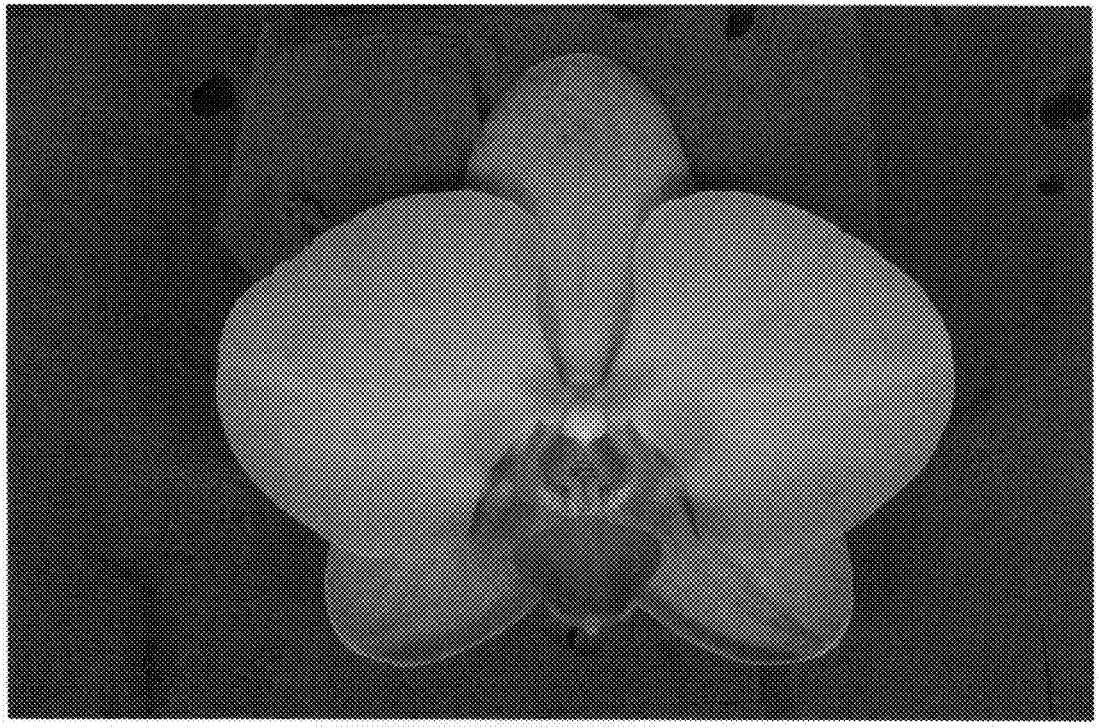
FIG. 2 shows a close-up of a flower of 'PHALDIQYK'.
Figure 3:
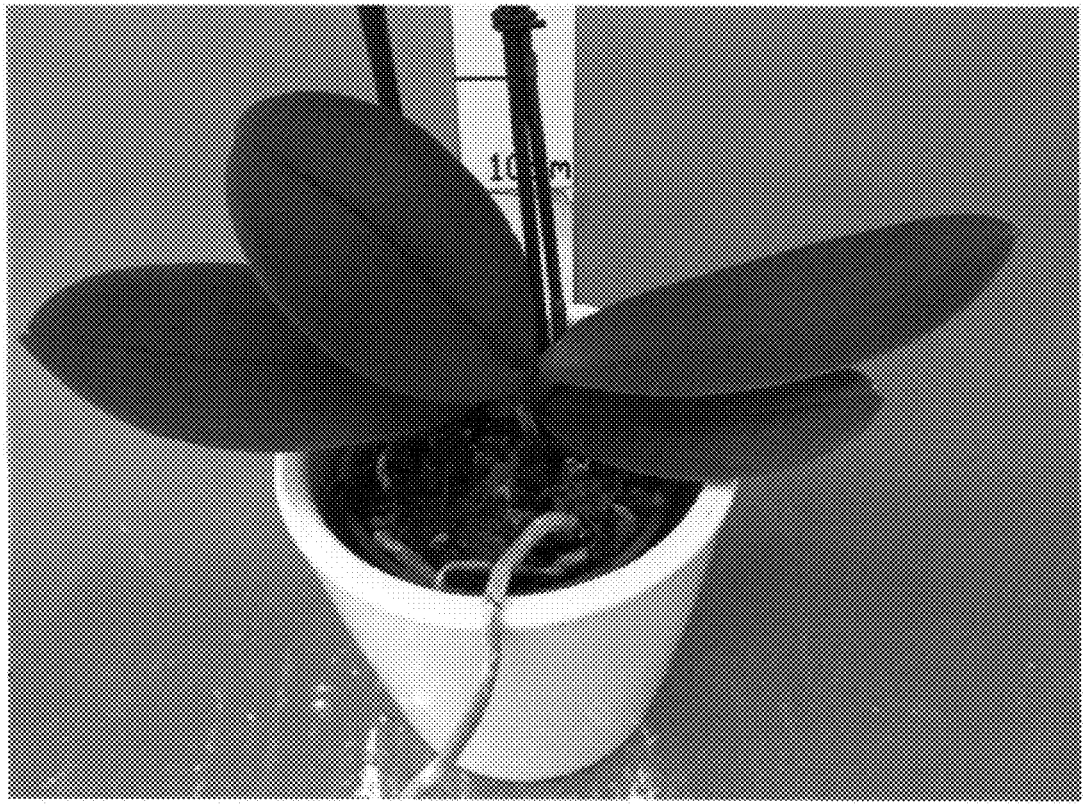
FIG. 3 shows a close-up of the leaves of 'PHALDIQYK'.

The following detailed description sets forth the distinctive characteristics of 'PHALDIQYK'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in May 2014. Color readings were taken under 4-6000 lux natural light in the greenhouse. Color references are primarily to The R.H.S. Colour Chart of The Royal Horticultural Society of London (R.H.S.) (1995 and 2015).

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDIQYK'.

Parentage:

*Female parent*.—*Phalaenopsis* cultivar '22286-0004' (unpatented).

*Male parent*.—*Phalaenopsis* cultivar '08815-0001' (unpatented).

Propagation:

*Type*.—Meristem tissue culture.

Plant:

*Crop time* (*time to produce a finished flowering plant*).—48 to 50 weeks for a 12 cm pot.

*Growth habit of inflorescence*.—Standard, green leaves and raceme to panicle.

*Height* (*including pot, including inflorescence*).—58.0 cm to 68.0 cm.

*Width* (*measured from leaf tips*).—26.0 cm to 33.0 cm.

*Vigor*.—Moderate.

Roots:

*Root description*.—Grey-green-colored roots with light branching lateral roots having grey-green-colored root tips.

Leaves:

*Mature leaves*.—Quantity per plant: 6 to 7 leaves are produced before flowering. Length (fully expanded): 12.0 cm to 17.0 cm. Width: 7.0 cm to 8.0 cm. Shape: Narrow oblong. Apex: Unequal mucronate. Leaf blade angle with the petiole: Between 15 degrees and 30 degrees. Leaf margin: Entire. Color: Upper surface: RHS 147A. Lower surface: RHS 146B. Texture: Slightly rough. Thickness: 2.6 mm. Venation: Pattern: Parallel. Color of the midvein: Upper surface: RHS 147A. Lower surface: RHS 146A.

Peduncle:

*Quantity per plant*.—1 to 2.

*Number of flowers per peduncle*.—8 to 11.

*Length*.—44.0 cm to 48.0 cm.

*Diameter*.—3.9 mm to 4.7 mm.

*Strength*.—Moderate.

*Aspect*.—Upright.

*Texture*.—Smooth.

*Color*.—Green (RHS 148A), and dark brown (RHS 200B) along the peduncle.

*Internode length*.—40.0 mm to 50.0 mm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 125.0 mm to 175.0 mm. Diameter of the peduncle at the inflorescence: 3.7 mm to 3.9 mm.

*Flowering time*.—First flowers can be expected 10 to 11 months after planting in a 12 cm pot.

*Flower bud*.—Length: 2.0 cm to 2.2 cm. Width: 1.5 cm to 1.7 cm. Shape: Egg shaped. Color: Greenish yellow (RHS 152C) and greyed-purple (RHS 184A).

*Flower*.—Height: 88.0 mm to 93.0 mm. Diameter: 90.0 mm to 100.0 mm. Depth of lip: 16.0 mm to 18.0 mm.

*Flower longevity*.—On the plant: 10 to 11 weeks.

*Fragrance*.—Absent.

*Petals*.—Arrangement: Open. Shape: Semi-circular. Apex: Rounded. Margin: Slightly undulate. Length (from base to tip): 46.0 mm to 48.0 mm. Width: 49.0 mm to 51.0 mm. Color (when newly opened): Upper surface: Main color: Red-purple (RHS 184D). At the base: Moderate yellow (RHS 161A). Lower surface: Main color: At the edge red-purple (RHS 186B). At the base: Moderate yellow (RHS 160A). Color (when fully opened): Upper surface: Main color: Red-purple (RHS 186B). At the base: Moderate yellow (RHS 161B). Lower surface: Main color: At the edge red-purple (RHS 186B). At the base: Moderate yellow (RHS 161B).

*Dorsal sepal*.—Shape: Elliptic. Margin: Entire. Length (from base to tip): 47.0 mm to 49.0 mm. Width: 32.0 mm to 34.0 mm. Color (when newly opened): Upper surface: Main color: Red-purple (RHS 184C). At the base: Moderate yellow (RHS 160B). Lower surface: Main color: Red-purple (RHS 186B). At the base: Moderate yellow (RHS 160A). Color (when fully opened): Upper surface: Main color: Red-purple (RHS 186B). At the base: Moderate yellow (RHS 161B). Lower surface: Main color: At the edge slightly red-purple (RHS 186B). At the base: Moderate yellow (RHS 160A).

*Lateral sepals*.—Shape: Ovate. Margin: Entire. Length (from base to tip): 47.0 mm to 49.0 mm. Width: 29.0 mm to 31.0 mm. Color (when newly opened): Upper surface: Main color: Red-purple (RHS 184C). At the base: Moderate yellow (RHS 161A). Lower surface: Main color: At the edge diluted red-purple (RHS 184C). At the base: Moderate yellow (RHS 160A). Color (when fully opened): Upper surface: Main color: Red-purple (RHS 184C). At the base: Moderate yellow (RHS 160B). Lower surface: Main color: At the edge diluted red-purple (RHS 186C). At the base: Moderate yellow (RHS 160A).

*Labellum* (*lip*).—Margin: The margins of lateral lobe and apical lobe are entire. Length: 17.0 mm to 19.0 mm. Width: 20.0 mm to 22.0 mm. Whiskers: Length: 1.0 cm to 1.2 cm. Color: Purple (RHS N78A) with yellow tips (RHS 2D).

*Lateral lobe*.—Length: 1.7 cm to 1.9 cm. Width: 0.7 cm to 0.9 cm. Shape: Type IV (as described in the International Union for the Protection of New Varieties of Plants (UPOV) Test Guidelines for *Phalaenopsis*). Color: Mix of red-purple (RHS 60B and RHS 185A); towards the callus slightly white (RHS NN155C) and yellow (RHS 12B).

*Apical lobe*.—Length: 2.0 cm to 2.2 cm. Width: 1.7 cm to 1.9 cm. Shape: Rhombic. Color: Red-purple (RHS 60B) and slightly yellow towards the callus (RHS 12A); purple (RHS N78A) towards the whiskers.

*Callus*.—Height: Moderately raised; 0.4 cm to 0.6 cm. Length: 0.4 cm to 0.6 cm. Width: 0.4 cm to 0.6 cm. Color: Yellow (RHS 15A) with red-purple dots (RHS 185A). Pubescence: None.

*Pedicel*.—Length: 37 mm to 39 mm. Diameter: 2.8 mm to 3.0 mm.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 11.0 mm to 13.0 mm. Diameter: 5.4 mm to 6.4 mm. Color: Lilac (RHS 78D).

*Pollinia*.—Quantity: 2. Size: 0.9 mm to 1.1 mm. Color: Orange (RHS 17A).

*Ovary*.—Length: 7.0 mm to 9.0 mm. Diameter: 2.4 mm to 2.8 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDIQYK' differs from female parent '22286-0004' (unpatented) in that 'PHALDIQYK' has red-purple flowers, whereas '22286-0004' has yellow flowers.

'PHALDIQYK' differs from male parent '08815-0001' (unpatented) in that 'PHALDIQYK' has a flower that is red-purple with yellow at the base, whereas '08815-0001' has a flower that is evenly pink. Additionally, 'PHALDIQYK' has a lateral lobe shape that is type IV and a smaller lip that is pink, whereas '08815-0001' has a lateral lobe shape that is type V and a bigger lip that is red/purple.

'PHALDIQYK' differs from commercial variety 'PHALCILAK' (unpatented) in that 'PHALDIQYK' has a flower that is evenly colored and a green-brown colored peduncle, whereas 'PHALCILAK' has a flower that is netted and center and a green colored peduncle. Additionally, 'PHALDIQYK' has a flower and lip that are bigger than those of 'PHALCILAK'.

I claim:

1. A new and distinct variety of *Phalaenopsis* plant named 'PHALDIQYK', substantially as illustrated and described herein.

* * * * *